United States Patent
Brister

(10) Patent No.: US 6,953,425 B2
(45) Date of Patent: Oct. 11, 2005

(54) METHOD OF TREATING VULNERABLE PLAQUE USING A CATHETER-BASED RADIATION SYSTEM

(75) Inventor: Mark Brister, Encinitas, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 10/829,561

(22) Filed: Apr. 22, 2004

(65) Prior Publication Data

US 2004/0242952 A1 Dec. 2, 2004

Related U.S. Application Data

(60) Provisional application No. 60/465,748, filed on Apr. 25, 2003.

(51) Int. Cl.[7] ................................................ A61N 5/00
(52) U.S. Cl. ...................................................... 600/3
(58) Field of Search ............................. 600/1–8; 606/27, 606/28, 32–34, 41, 43, 46; 607/96, 98–101, 103; 623/1.1, 1.11, 1.23, 902, 903; 128/898–899

(56) References Cited

U.S. PATENT DOCUMENTS

| | | |
|---|---|---|
| 5,213,561 A | 5/1993 | Weinstein et al. |
| 5,484,384 A | 1/1996 | Fearnot |
| 5,503,613 A | 4/1996 | Weinberger |
| 5,924,997 A | 7/1999 | Campbell |
| 6,228,109 B1 * | 5/2001 | Tu et al. ..................... 607/113 |
| 6,338,709 B1 | 1/2002 | Geoffrion et al. |
| 6,377,846 B1 | 4/2002 | Chornenky et al. |
| 6,475,159 B1 | 11/2002 | Casscells et al. |
| 6,475,210 B1 | 11/2002 | Phelps et al. |
| 6,554,758 B2 * | 4/2003 | Turnlund et al. .............. 600/3 |
| 6,786,904 B2 * | 9/2004 | Doscher et al. ............... 606/28 |

* cited by examiner

Primary Examiner—John P. Lacyk

(57) ABSTRACT

The invention provides a method of treating vulnerable plaque at a site in a vessel. A vulnerable plaque site is identified for treatment. A radiation source is introduced into a vessel containing a vulnerable plaque site identified for treatment. The radiation source is guided to a position adjacent to the treatment site. A therapeutically effective dose of radiation is delivered to the vulnerable plaque site. As the radiation impinges upon the wall of the lumen, it promotes cell growth. Such growth can serve to strengthen the thin fibrous cap found atop a vulnerable plaque lesion. With the lesion thus stabilized, time is provided for the use of statin drugs or other agents to shrink or remove the lipid pool beneath the cap.

30 Claims, 4 Drawing Sheets

METHOD OF TREATING VULNERABLE PLAQUE USING A CATHETER-BASED RADIATION SYSTEM

RELATED APPLICATION

This application claims priority to U.S. Provisional Application No. 60/465,748, "Method of Treating Vulnerable Plaque Using a Catheter-based Radiation System" to Mark Brister, filed Apr. 25, 2003, the entirety of which is incorporated by reference.

TECHNICAL FIELD

This invention relates generally to treatment of coronary artery disease. More specifically, the invention relates to treatment of vulnerable plaque using a catheter-based radiation system.

BACKGROUND OF THE INVENTION

Heart disease, specifically coronary artery disease, is a major cause of death, disability, and healthcare expense in the United States and other industrialized countries. Until recently, most heart disease was considered to be primarily the result of a progressive increase of hard plaque in the coronary arteries. This atherosclerotic disease process of hard plaques leads to a critical narrowing (stenosis) of the affected coronary artery and produces anginal syndromes, known commonly as chest pain. The progression of the narrowing reduces blood flow, triggering the formation of a blood clot (thrombus). The clot may choke off the flow of oxygen-rich blood (ischemia) to heart muscles, causing a heart attack. Alternatively, the clot may break off and lodge in the vessel of another organ, such as the brain, resulting in a thrombotic stroke. Within the past decade, evidence has emerged changing the paradigm of atherosclerosis, coronary artery disease, and heart attacks. While the buildup of hard plaque may produce angina and severe ischemia in the coronary arteries, new clinical data suggest that the rupture of vulnerable plaques, which are often non-occlusive, per se, causes the vast majority of heart attacks. The rate is estimated as high as 60–80 percent.

In many instances, vulnerable plaques do not impinge on the vessel lumen; rather, much like an abscess, they are ingrained within the arterial wall. The majority of vulnerable plaques include a lipid pool, smooth muscle (endothelial) cells, and a dense infiltrate of macrophages contained by a thin fibrous cap. The lipid pool is believed to be formed as a result of pathological process involving low density lipoprotein (LDL), macrophages, and the inflammatory process. The macrophages oxidize the LDL, producing foam cells.

The macrophages, foam cells, and associated endothelial cells release various substances, such as tumor necrosis factor, tissue factor, and matrix proteinases, which result in generalized cell necrosis and apoptosis, pro-coagulation, and weakening of the fibrous cap. The inflammation process may weaken the fibrous cap to the extent that sufficient mechanical stress, such as that produced by increased blood pressure, may result in rupture. The lipid core and other contents of the vulnerable plaque may then spill into the blood stream, thereby initiating a clotting cascade. The cascade produces a blood clot that potentially results in a heart attack and/or stroke. The process is exacerbated due to the release of collagen and plaque components (e.g., collagen and tissue factor), which enhance clotting upon their release.

Various methods of identifying vulnerable plaques have been proposed. These include sensing the temperature differential between healthy vascular tissue and the inflamed tissue of a vulnerable plaque. Devices that identify vulnerable plaques by the higher temperature of the inflamed tissue have been described in, for example, U.S. Pat. No. 5,924,997 to Campbell and U.S. Pat. No. 6,475,159 to Casscells, et al. A spectrographic identification method for vulnerable plaques is described in U.S. Pat. No. 6,475,210 to Phelps, et al.

Currently there are few strategies for reliably treating vulnerable plaques. Percutaneous transluminal coronary angioplasty (PTCA), which is commonly used to treat hard plaques, is contraindicated. In this procedure, a catheter having an inflatable balloon at its distal end is introduced into the coronary artery, and the balloon is inflated to flatten the hard plaque against the arterial wall. Inflation of a balloon catheter near a vulnerable plaque could rupture the thin fibrous cap covering the lipid pool, resulting in precisely the clotting cascade that treatment would seek to prevent. However, radiation treatment, which has been used to prevent the restenosis that sometimes occurs following PTCA, holds promise in treating vulnerable plaques.

While high levels of radiation inhibit stenosis, lower levels appear to promote cell growth and encourage restenosis. For example, hyperplasia has been seen to occur at the distal and proximal edges of a treated area due to reduced radiation exposure at these edges. The resulting stenosis at either end of the treated area is termed a "candy-wrapper" effect.

Thickening of the inner wall of a vessel is clearly an unwanted and deleterious side effect when treating hard plaques. However, such thickening could have a positive effect when it serves to strengthen the thin fibrous cap found atop a vulnerable plaque lesion. With the lesion thus stabilized, time is provided for the use of statin drugs or other agents to shrink or remove the lipid pool.

Radiation therapy can be accomplished in a variety of ways, as discussed, for example, in U.S. Pat. No. 5,213,561 to Weinstein et al., U.S. Pat. No. 5,484,384 to Fearnot, and U.S. Pat. No. 5,503,613 to Weinberger. Among other radiation therapy devices, these references disclose a guide wire having a radioactive tip, a radioactive source within a balloon catheter, and a radioactive source mounted on a balloon expansible stent. In U.S. Pat. No. 6,377,846 B1, Chornenky et al. disclose an improved device for delivering localized x-ray radiation and a method for fabricating such a device.

It would be desirable to have a method of treating vulnerable plaques that overcomes the clear disadvantages of traditional methods of plaque treatment such as PTCA, while realizing the benefits of radiation therapy.

SUMMARY OF THE INVENTION

One aspect of the present invention is a method of treating vulnerable plaque at a site in a vessel. A vulnerable plaque site is identified for treatment. A radiation source is introduced into a vessel containing the vulnerable plaque site identified for treatment. The radiation source is guided to a position adjacent to the identified treatment site. A therapeutically effective dose of radiation is then delivered to the identified vulnerable plaque site.

Prior to carrying out the above steps, a percutaneous access site may be made into a vessel to be treated or a vessel that leads to a vessel to be treated. A guiding catheter may be advanced through the percutaneous access site to the vulnerable plaque site identified for treatment.

After a therapeutically effective dose of radiation has been delivered to the vulnerable plaque site identified for treatment, the radiation source may be withdrawn from the vessel.

Another aspect of the present invention is a system for treating vulnerable plaque at a site in a vessel. The system comprises means for identifying a vulnerable plaque site for treatment, introducing a radiation source into a vessel containing the vulnerable plaque site identified for treatment, guiding the radiation source to a position adjacent to the vulnerable plaque site identified for treatment, and delivering a therapeutically effective dose of radiation to the vulnerable plaque site identified for treatment. The treatment system may also comprise means for first making a percutaneous access site into a vessel to be treated or a vessel that leads to a vessel to be treated and advancing a guiding catheter through the percutaneous access site to the vulnerable plaque site identified for treatment. The system may further comprise means for withdrawing the radiation source from the vessel after a therapeutically effective dose of radiation has been delivered to the vulnerable plaque site identified for treatment.

The aforementioned and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE PRESENTLY PREFERRED EMBODIMENTS

Figure 1:
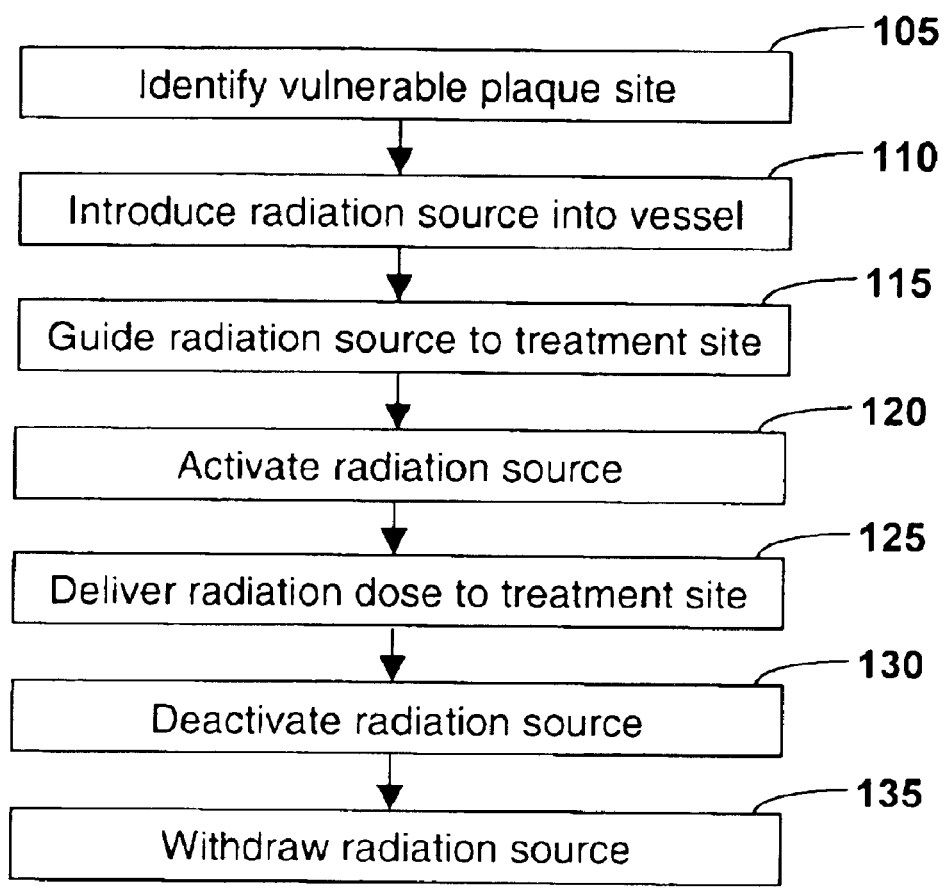
FIG. 1 is a flow diagram of one embodiment of a method of treating vulnerable plaque at a site in a vessel, in accordance with the present invention.

One aspect of the present invention is a method of treating vulnerable plaque at a site in a vessel. FIG. 1 shows a flow diagram of one embodiment of the method at 100, in accordance with the present invention.

A vulnerable plaque site may be identified for treatment (Block 105). Identification is an important element in treating vulnerable plaques because it permits treatment to be delivered to a precise location. Identification may be accomplished using methods such as thermography or spectrography.

A catheter-based radiation source may be introduced into the vessel containing the vulnerable plaque site identified for treatment (Block 110). The radiation source may be, for example, a radioactive wire, a radioactive strip, a radioactive pellet, a radioactive stent, a receptacle or lumen that contains radioactive material, a receptacle or lumen that receives radioactive material, a receptacle or lumen that is coated with radioactive material, a device for delivering x-ray radiation, and the like. The radiation source may be guided to a position adjacent to the treatment site (Block 115).

The radiation source may be activated, for example by withdrawing a sheath covering the radiation source or by providing voltage to a device for delivering localized x-ray radiation (Block 120). The present embodiment is not limited to a particular x-ray device; however, the invention is especially useful with the device described in U.S. Pat. No. 6,377,846 B1, incorporated herein by reference.

A therapeutically effective dose of radiation, for example 5–20 Gray (Gy), may be delivered to the vulnerable plaque site identified for treatment (Block 125). As the radiation impinges upon the wall of the lumen, it promotes cell growth. Such growth can serve to strengthen the thin fibrous cap found atop a vulnerable plaque lesion, preventing or postponing rupture of the cap and providing time for the use of statin drugs or other agents to shrink or remove the lipid pool beneath the cap.

If the radiation source is a radioactive stent, the source may be left in place within the vessel. Otherwise, the source may be deactivated (Block 130) and withdrawn (Block 135) after a therapeutically effective dose of radiation has been delivered to the vulnerable plaque site.

Figure 2:
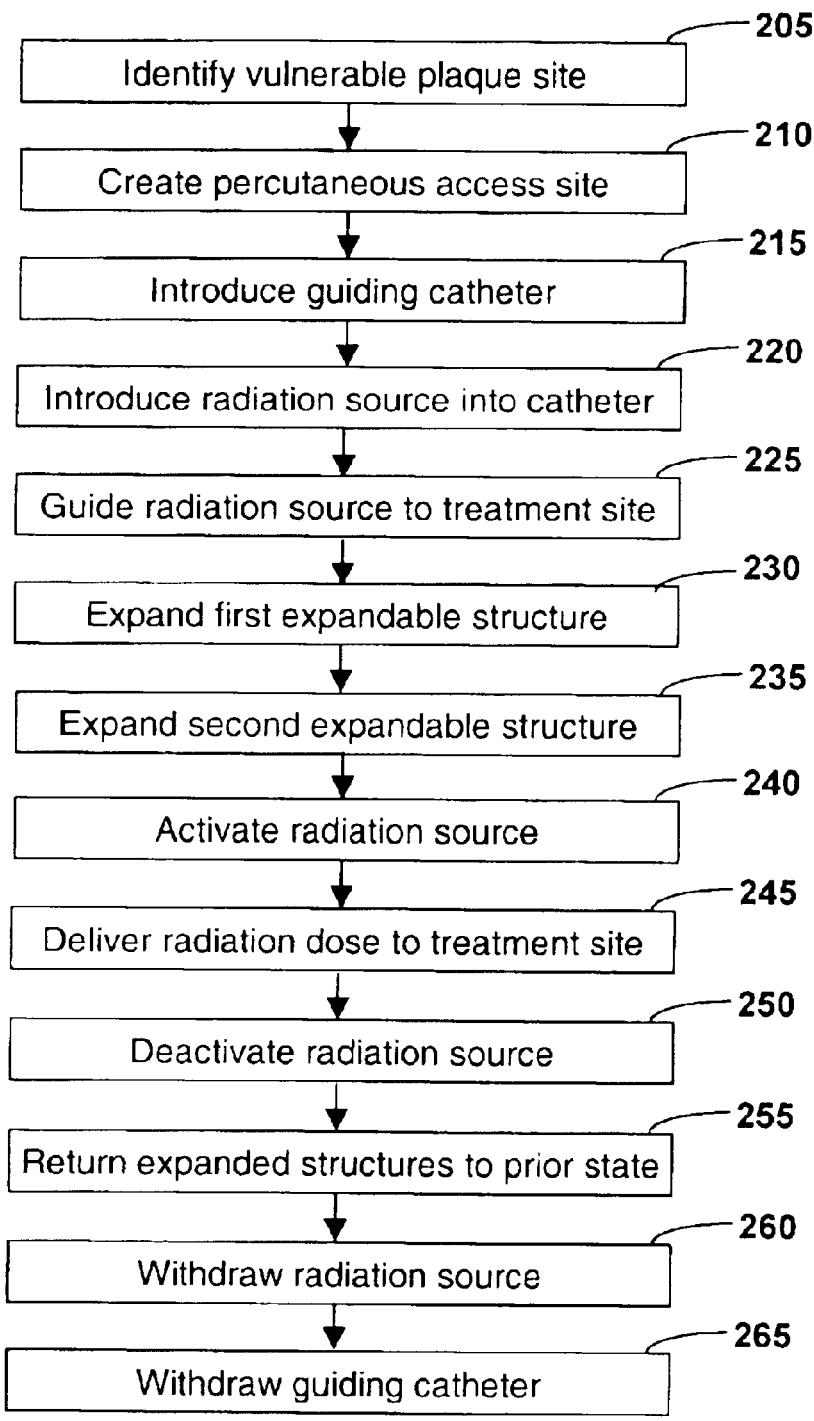
FIG. 2 is a flow diagram of another embodiment of a method of treating vulnerable plaque at a site in a vessel, in accordance with the present invention.

Another embodiment of the method, in accordance with the present invention, is diagrammed in FIG. 2 at 200.

A vulnerable plaque site may be identified for treatment (Block 205). Identification is an important element in treating vulnerable plaques because it permits treatment to be delivered to a precise location. Identification may be accomplished using methods such as thermography or spectrography.

A percutaneous access site may be created in the vessel to be treated or a vessel that leads to the vessel to be treated (Block 210). A guiding catheter may be introduced through the percutaneous access site and advanced to a position that is adjacent to the vulnerable plaque site identified for treatment (Block 215).

A catheter-based radiation treatment device may be introduced into the guiding catheter, either over a guide wire or directly into the guiding catheter (Block 220). The radiation treatment device may be guided to the vulnerable plaque site identified for treatment (Block 225).

An expandable structure such as a balloon that is included on the radiation device may be expanded distal to the vulnerable plaque site identified for treatment (Block 230). The structure should be adequately expanded such that it contacts the vessel walls without damaging tissue or rupturing the vulnerable plaque lesion. A second expandable structure included on the radiation device may be similarly expanded proximal to the vulnerable plaque site identified for treatment (Block 235).

The one or more expandable structures may serve to center the radiation device in the vessel. Centering the device may provide more uniform exposure of the vessel walls to radiation emitted by the device. The present embodiment is not limited to a particular means of centering a catheter-based radiation device within a vessel. However, the invention is especially useful with the means described in U.S. Pat. No. 6,338,709 B1, incorporated herein by reference.

The one or more expandable structures may be fabricated of a material that is capable of substantially shielding the area of the vessel distal and proximal to the vulnerable plaque site from unwanted radioactive exposure.

The radiation treatment device may be activated, for example by withdrawing a sheath covering the radiation source or by providing power to a device for delivering localized x-ray radiation (Block 240). The present embodiment is not limited to a particular x-ray device; however, the invention is especially useful with the x-ray device described in U.S. Pat. No. 6,377,846 B1, incorporated herein by reference.

A therapeutically effective dose of radiation, for example 5–20 Gray (Gy), may then be delivered to the vulnerable plaque site identified for treatment (Block 245). After a therapeutically effective dose of radiation has been delivered to the vulnerable plaque site, the radiation treatment device may be deactivated, for example by resheathing the radiation source or by discontinuing power to the x-ray radiation device (Block 250).

The one or more expandable structures included on the radiation device may be returned to an unexpanded state (Block 255), and the catheter-based radiation treatment device may be withdrawn from the vessel (Block 260). The guiding catheter may also be withdrawn from the vessel (Block 265).

Figure 3:
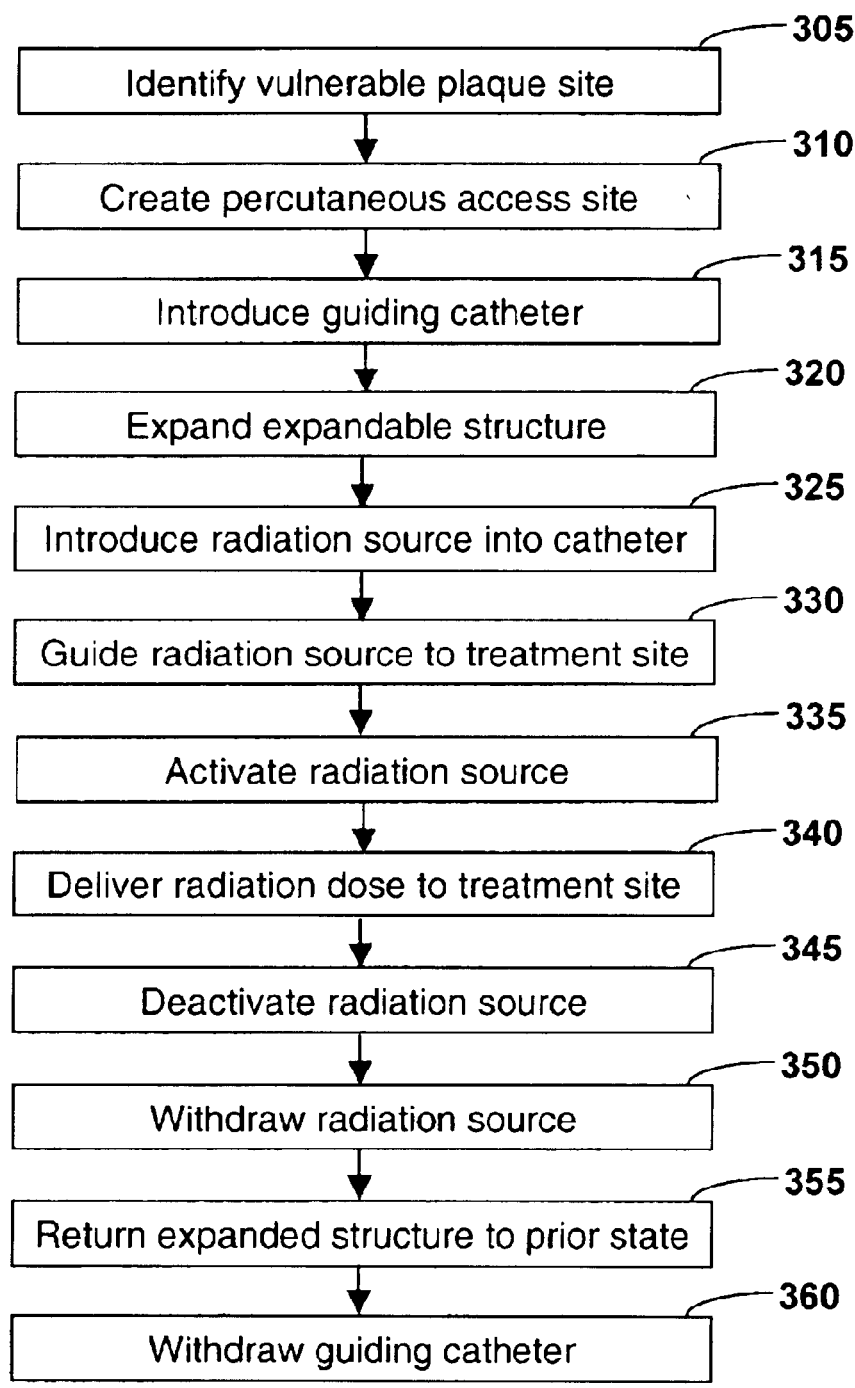
FIG. 3 is a flow diagram of another embodiment of a method of treating vulnerable plaque at a site in a vessel, in accordance with the present invention.

Yet another embodiment of the method, in accordance with the present invention, is diagrammed in FIG. 3 at 300.

A vulnerable plaque site may be identified for treatment (Block 305). Identification is an important element in treating vulnerable plaques because it permits treatment to be delivered to a precise location. Identification may be accomplished using methods such as thermography or spectrography.

A percutaneous access site may be created in either the vessel to be treated or a vessel that leads to the vessel to be treated (Block 310). A guiding catheter may be introduced through the percutaneous access site and advanced to a position that is adjacent and distal to the vulnerable plaque site identified for treatment (Block 315).

An expandable structure at the distal end of the guiding catheter, for example a balloon, may be expanded such that it contacts the vessel walls without damaging tissue, thereby centering the guiding catheter in the vessel (Block 320). The expandable structure may be fabricated of a material that is capable of substantially shielding the area of the vessel distal to the guiding catheter from unwanted radioactive exposure.

A catheter-based radiation treatment device may be introduced into the guiding catheter, either over a guide wire or directly into the guiding catheter (Block 325). The radiation treatment device may be guided to the vulnerable plaque site identified for treatment (Block 330). The radiation treatment device may be activated, for example by withdrawing a sheath covering the radiation source or by providing power to a device for delivering localized x-ray radiation (Block 335). The present embodiment is not limited to a particular x-ray device. However, the invention is especially useful with the x-ray device described in U.S. Pat. No. 6,377,846 B1, incorporated herein by reference.

A therapeutically effective dose of radiation, for example 5–20 Gray (Gy), may then be delivered to the vulnerable plaque site identified for treatment (Block 340). The radiation treatment device may be held stationary while irradiating the vessel, or it may be moved axially to treat the entire area of vulnerable plaque. If the treatment device is held stationary while irradiating the vessel, a second expandable shielding structure positioned on the treatment device proximal to the radiation source may be expanded to substantially shield the area of the vessel proximal to the intended treatment area from unwanted radioactive exposure.

After a therapeutically effective dose of radiation has been delivered to the vulnerable plaque site, the radiation treatment device may be deactivated, for example by resheathing the radiation source or by discontinuing power to the x-ray radiation device (Block 345). The catheter-based radiation treatment device may then be withdrawn from the vessel (Block 350) after returning any expandable structure to its unexpanded state.

The expandable structure at the distal end of the guiding catheter may be returned to an unexpanded state (Block 355), and the guiding catheter may be withdrawn (Block 360).

Figure 4:
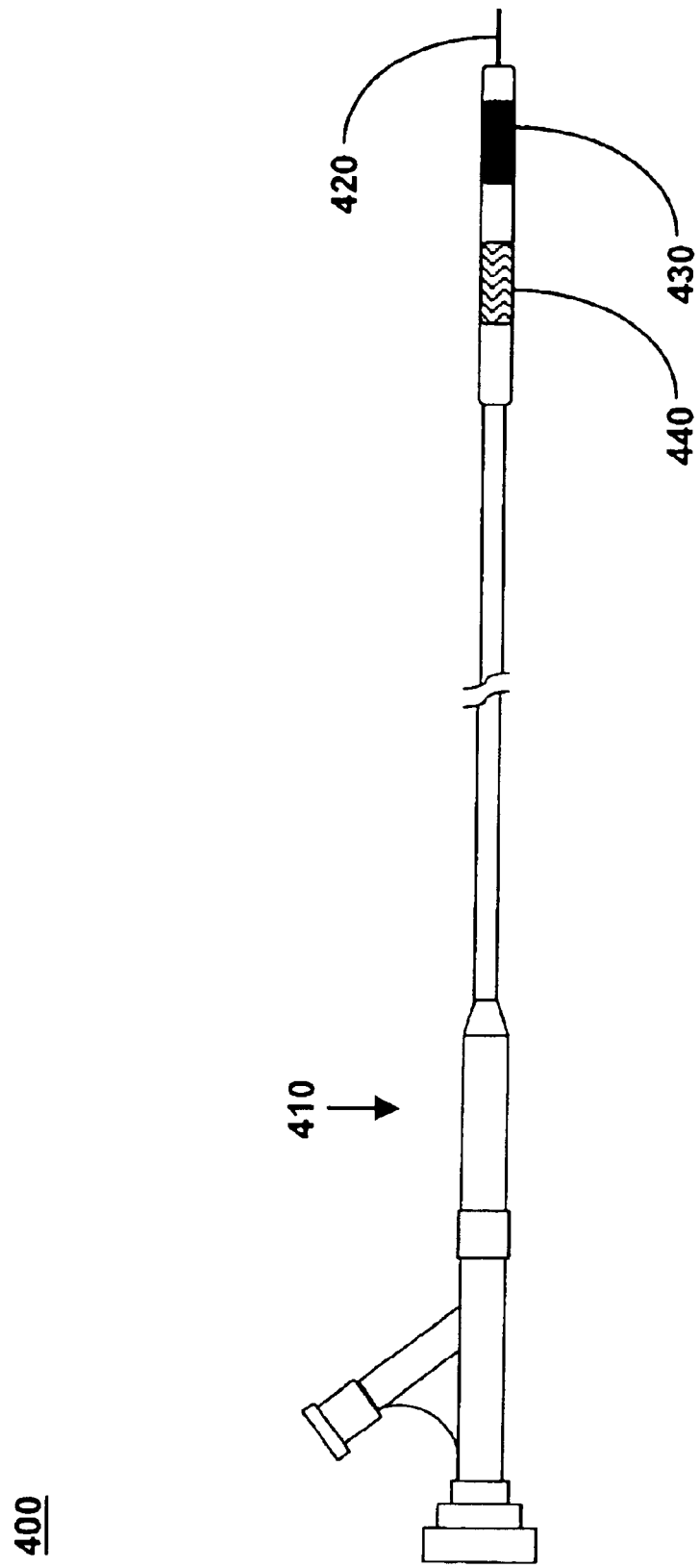
FIG. 4 is an illustration of one embodiment of a system for treating vulnerable plaque at a site in a vessel, in accordance with the current invention.

FIG. 4 shows one embodiment of a system for treating vulnerable plaque at a site in a vessel, in accordance with the current invention, at 400.

System 400 contains a catheter 410, a guide wire 420, a device for identifying a vulnerable plaque site 430, and a radiation source 440.

A single catheter 410 is shown in FIG. 4 carrying both the identification device 430 and the radiation source 440. However, identification device 430 and radiation source 440 may be carried on two separate catheters.

Identification device 430 is used to identify a vulnerable plaque site for treatment. Identification may be accomplished using methods such as thermography or spectrography.

Radiation source 440 may be, for example, the x-ray device described in U.S. Pat. No. 6,377,846 B1, incorporated herein by reference. Alternatively, it may be any appropriate radiation source capable of delivering a therapeutically effective dose of radiation to the vulnerable plaque site identified for treatment. In this embodiment, a guide wire 420 is used to guide the radiation source to a position adjacent to the vulnerable plaque site identified for treatment.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A method of treating vulnerable plaque at a site in a vessel, comprising:

identifying a vulnerable plaque site for treatment;

introducing a radiation source into a vessel containing a vulnerable plaque site identified for treatment;

guiding the radiation source to a position adjacent to the vulnerable plaque site identified for treatment; and delivering a therapeutically effective dose of radiation to the vulnerable plaque site identified for treatment, wherein a retractable shield surrounds the radiation source when the vessel is not being treated.

2. The method of claim 1 wherein the radiation source is selected from a group consisting of a radioactive wire, a radioactive strip, a radioactive pellet, a radioactive stent, a receptacle or lumen that contains radioactive material, a receptacle or lumen that receives radioactive material, a receptacle or lumen that is coated with radioactive material, and a device for delivering x-ray radiation.

3. The method of claim 1 further comprising:

first making a percutaneous access site into one of a vessel to be treated or a vessel that leads to a vessel to be treated and advancing a guiding catheter through the percutaneous access site to the vulnerable plaque site identified for treatment.

4. The method of claim 3 wherein the guiding catheter includes a guide wire at least partially enclosed by the guiding catheter.

5. The method of claim 4 wherein the radiation source is introduced over the guide wire.

6. The method of claim 4 wherein the guide wire is withdrawn prior to introducing the radiation source.

7. The method of claim 3 wherein the guiding catheter includes at least one expandable structure adjacent a distal end of the catheter.

8. The method of claim 7 wherein the expandable structure is a balloon.

9. The method of claim 7 wherein the expandable structure is expanded prior to delivering a therapeutically effective dose of radiation to the vulnerable plaque site identified for treatment.

10. The method of claim 9 wherein the expanded structure is in contact with the vessel to be treated at a location adjacent and distal to the vulnerable plaque site identified for treatment.

11. The method of claim 9 wherein the expanded structure centers the guiding catheter within the vessel to be treated.

12. The method of claim 9 wherein the expanded structure shields the vessel to be treated from radiation exposure distal to the vulnerable plaque site identified for treatment.

13. The method of claim 9 wherein the expandable structure is returned to an unexpanded state after a therapeutically effective dose of radiation has been delivered to the vulnerable plaque site identified for treatment.

14. The method of claim 1 wherein the radiation source comprises at least one element of a radiation treatment device.

15. The method of claim 14 wherein the radiation treatment device includes at least one expandable structure.

16. The method of claim 15 wherein the expandable structure is expanded prior to delivering a therapeutically effective dose of radiation to the vulnerable plaque site identified for treatment.

17. The method of claim 15 wherein the expandable structure is a balloon.

18. The method of claim 15 wherein the expandable structure shields the vessel to be treated from radiation exposure beyond the vulnerable plaque site identified for treatment.

19. The method of claim 15 wherein the expandable structure is returned to an unexpanded state after a therapeutically effective dose of radiation has been delivered to the vulnerable plaque site identified for treatment.

20. The method of claim 15 wherein the expandable structure is adjacent to a proximal end of the radiation source.

21. The method of claim 20 wherein the expandable structure is positioned within the vessel to be treated at a location adjacent and proximal to the vulnerable plaque site identified for treatment.

22. The method of claim 15 wherein the expandable structure is adjacent to a distal end of the radiation source.

23. The method of claim 22 wherein the expandable structure is positioned within the vessel to be treated at a location adjacent and distal to the vulnerable plaque site identified for treatment.

24. The method of claim 15 wherein at least one expandable structure is adjacent to a distal end of the radiation source and at least one expandable structure is adjacent to a proximal end of the radiation source.

25. The method of claim 24 wherein at least one expandable structure is positioned within the vessel to be treated at a location adjacent and distal to the vulnerable plaque site identified for treatment and at least one expandable structure is positioned within the vessel to be treated at a location adjacent and proximal to the vulnerable plaque site identified for treatment.

26. The method of claim 1 wherein delivering a therapeutically effective dose of radiation to the vulnerable plaque site identified for treatment comprises positioning the radiation source at the vulnerable plaque site and exposing the vessel to radiation while the device is stationary.

27. The method of claim 1 wherein delivering a therapeutically effective dose of radiation to the vulnerable plaque site identified for treatment comprises positioning the radiation source at a point adjacent a distal edge of the vulnerable plaque site and exposing the vessel to radiation while the device is moved axially to treat the entire area of plaque.

28. The method of claim 1 further comprising:
  withdrawing the radiation source from the vessel after a therapeutically effective dose of radiation has been delivered to the vulnerable plaque site identified for treatment.

29. A method of treating vulnerable plaque at a site in a vessel, comprising:
  identifying a vulnerable plaque site for treatment;
  advancing a guiding catheter to the vulnerable plaque site identified for treatment, the guiding catheter having at least one expandable structure adjacent a distal end of the catheter;
  introducing a radiation source into a vessel containing a vulnerable plaque site identified for treatment;
  guiding the radiation source to a position adjacent to the vulnerable plaque site identified for treatment;
  expanding the expandable structure; and
  delivering a therapeutically effective dose of radiation to the vulnerable plaque site identified for treatment, wherein the expanded structure shields the vessel to be treated from radiation exposure distal to the vulnerable plaque site identified for treatment.

30. A method of treating vulnerable plaque at a site in a vessel, comprising:
  identifying a vulnerable plaque site for treatment;
  advancing a guiding catheter to the vulnerable plaque site identified for treatment;
  introducing a radiation source into a vessel containing a vulnerable plaque site identified for treatment, the radiation source comprising at least one element of a radiation treatment device, the radiation treatment device including at least one expandable structure;
  guiding the radiation source to a position adjacent to the vulnerable plaque site identified for treatment;
  expanding the expandable structure; and
  delivering a therapeutically effective dose of radiation to the vulnerable plaque site identified for treatment, wherein the expanded structure shields the vessel to be treated from radiation exposure beyond the vulnerable plaque site identified for treatment.

* * * * *